(12) United States Patent
Castagna et al.

(10) Patent No.: US 12,370,137 B2
(45) Date of Patent: Jul. 29, 2025

(54) METHOD AND COMPOSITION FOR TREATING OBESITY

(71) Applicant: MannKind Corporation, Westlake Village, CA (US)

(72) Inventors: Michael Castagna, Westlake Village, CA (US); David Kendall, Westlake Village, CA (US); Kelly Kraft, Poughquag, NY (US); Chad C. Smutney, Watertown, CT (US); Marshall Grant, Newtown, CT (US)

(73) Assignee: MannKind Corporation, Danbury, CT (US)

( * ) Notice: Subject to any disclaimer, the term of this patent is extended or adjusted under 35 U.S.C. 154(b) by 986 days.

(21) Appl. No.: 17/077,754

(22) PCT Filed: Apr. 25, 2019

(86) PCT No.: PCT/US2019/029166
§ 371 (c)(1),
(2) Date: Oct. 22, 2020

(87) PCT Pub. No.: WO2019/210083
PCT Pub. Date: Oct. 31, 2019

(65) Prior Publication Data
US 2021/0259963 A1 Aug. 26, 2021

Related U.S. Application Data

(60) Provisional application No. 62/663,842, filed on Apr. 27, 2018.

(51) Int. Cl.
| | |
|---|---|
| *A61K 31/495* | (2006.01) |
| *A61K 9/00* | (2006.01) |
| *A61K 31/198* | (2006.01) |
| *A61K 38/28* | (2006.01) |
| *A61K 45/06* | (2006.01) |

(52) U.S. Cl.
CPC .......... *A61K 9/0075* (2013.01); *A61K 31/198* (2013.01); *A61K 31/495* (2013.01); *A61K 38/28* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 8,785,396 B2 | 7/2014 | Leone-Bay et al. | |
| 2010/0203014 A1* | 8/2010 | Maggio ................ | A61K 9/0043 514/4.8 |
| 2014/0199398 A1* | 7/2014 | Grant ........................ | A61P 3/10 544/383 |
| 2015/0174209 A1* | 6/2015 | Chiquette .............. | G16H 20/17 604/151 |

FOREIGN PATENT DOCUMENTS

CN    103800301 A  *  5/2014

OTHER PUBLICATIONS

Yang et al., "Prevalence and risk factors for type 2 diabetes mellitus with Prader-Willi syndrome: a single center experience", Orphanet Journal of Rare Diseases, 2017, vol. 12:146, pp. 1-9.
Angelo et al., "Technosphere® Insulin: Defining the Role of Technosphere Particles at the Cellular Level", Journal of Diabetes Science and Technology, vol. 3, Issue 3, May 2009, pp. 545-554.
Potocka et al, "Pharmacokinetic Characterization of the Novel Pulmonary Delivery Excipient Fumaryl Diketopiperazine", Journal of Diabetes Science and Technology, vol. 4, Issue 5, Sep. 2010, pp. 1164-1173.
International Search Report mailed on Sep. 16, 2019 for International Application No. PCT/US2019/29166 filed on Apr. 25, 2019.

\* cited by examiner

*Primary Examiner* — Alton N Pryor
(74) *Attorney, Agent, or Firm* — K&L Gates LLP; Brian J. Novak; Hal Gibson

(57) ABSTRACT

A method for treating obesity associated to Prader Willi Syndrome and/or binge eating is disclosed. The method utilizes a rapid drug delivery system which delivers small molecules and peptides to the lungs by oral inhalation.

12 Claims, No Drawings

METHOD AND COMPOSITION FOR TREATING OBESITY

CROSS REFERENCE TO RELATED APPLICATIONS

This application is a national stage application of PCT/US19/29166, filed Apr. 25, 2019, which claims the benefit of provisional patent application No. 62/663,842, filed Apr. 27, 2018, the entire contents of which are incorporated herein by reference.

TECHNICAL FIELD

Method and composition for treating obesity and hyperglycemia are disclosed. The method comprises administering to a subject a pharmaceutical formulation comprising an endocrine hormone or an analog thereof, alone or in combination with other active agents, including other endocrine hormones. In particular, the composition is for administration to a patient in need of treatment using a drug delivery system for pulmonary inhalation.

BACKGROUND

Obesity is a major disorder affecting a large number of the population worldwide. It can develop from multiple factors, including genetic and metabolic disorders and/or overeating. A large subset of the population struggles with obesity resulting from eating disorders, for example, excessive dieting fluctuations, loss of control in eating, excessive, or binge eating, anxiety and depression.

An example of morbid obesity occurs in subjects with Prader-Willi syndrome (PWS), which is a genetic disorder with onset in childhood and typically occurs from new chromosomal mutations, and/or loss of function of specific genes, in particular, chromosome 15. PWS can cause excessive obesity and often leads to type 2 diabetes. The disorder is usually diagnosed in newborns who exhibit symptoms, including hypotonia/poor muscle tone, poor feeding, weak sucking reflex and slow development. The disorder progresses from infancy and the subjects can exhibit abnormal neurologic function, hypogonadism, developmental and cognitive delays, hyperphagia and obesity. There are multiple side effects with the disorder including, mild to moderate intellectual impairment and behavioral problems. In childhood this can lead to social and behavioral problems at school and other settings affecting not only the subject but the entire family. PWS has no cure and affects about 1 in 10,000 and 30,000 people; males and females are affected equally.

Symptoms associated with subjects affected with PWS can be mild to severe and include, constant, extreme, ravenous, insatiable appetite which persists no matter how much the patient eats, and often results in morbid obesity. It is the most common genetic cause of morbid obesity in children. It has been reported that in the hypothalamus of people with PWS, nerve cells that produce oxytocin, a hormone thought to contribute to satiety, have been found to be abnormal.

If diagnosis of the disease occurs early, and treatment begins early after detection, it can improve the disorder outcomes. Subjects diagnosed with PWS are prescribed daily recombinant growth hormone injections. It is always recommended that children diagnosed with PWS follow strict food intake guidelines, such as limiting food intake and access to food early on, starting around three years of age and supplementing their daily activities with an exercise regime and counseling, specifically for those subjects exhibiting behavioral issues, including, tantrums and obsessive compulsive disorder, which are commonly associated symptoms. Growth hormone therapy has been shown to work by improving outcomes, such as improved bone density and muscle mass, and may lessen food preoccupation and weight gain. Treatment in adults may include, appetite suppressant therapy, strict dietetic regimens and isolation/participation in group homes, which are often necessary to avoid food temptation. PWS symptoms related to behavior are treated with, for example, serotonin receptor agonists, which are mostly effective in lessening temper tantrums and improving compulsivity, however, new methods of treatment to further ameliorate and suppress a subject's appetite and that would provide better control of the disorder and associate symptoms are still needed.

Drug delivery systems for the administration of therapeutically active ingredients or agents into the circulation are numerous and include, oral, transdermal, subcutaneous and intravenous injections. While these systems have been used for quite a long time and can deliver sufficient medication for the treatment of many diseases, there are numerous challenges associated with these drug delivery mechanisms. In particular, delivery of effective amounts of, for example, proteins and peptides to treat a target disease has been problematic. Many factors are involved in introducing the right amount of the active agent into the circulation, including, preparation of the proper drug delivery formulation so that the formulation contains an amount of active agent that can reach its site(s) of action in an effective amount.

The active agent must be stable in the drug delivery formulation and the formulation should allow for absorption of the active agent into the circulation and remain active so that it can reach the target site(s) of action at effective therapeutic levels while minimizing the amount of dose to be administered. Thus, in the pharmacological arts, drug delivery systems which can deliver a stable active agent are of utmost importance.

Making drug delivery formulations therapeutically suitable for treating disease depends on the characteristics of the active ingredient or agent to be delivered to the patient. Such characteristics can include in a non-limiting manner solubility, pH, stability, toxicity, release rate, and ease of removal from the body by normal physiologic processes. For example, in oral administration, if the agent is sensitive to acid, enteric coatings have been developed using pharmaceutically acceptable materials which can prevent the active agent from being released in the low pH (acid) of the stomach. Thus, polymers that are not soluble at acidic pH are used to formulate and deliver a dose containing acid-sensitive agents to the small intestine where the pH is neutral. At neutral pH, the polymeric coating can dissolve to release the active agent which is then absorbed into the enteric systemic circulation. Orally administered active agents enter the systemic circulation and pass through the liver. In certain cases, some portion of the dose is metabolized and/or deactivated in the liver before reaching the target tissues. In some instances, the metabolites can be toxic to the patient, or can yield unwanted side effects.

Similarly, subcutaneous and intravenous administration of pharmaceutically-active agents is not devoid of degradation and inactivation. With intravenous administration of drugs, the drugs or active ingredients can be metabolized, for example in the liver, before reaching the target tissue. With subcutaneous administration of certain active agents, including various proteins and peptides, there is additionally degradation and deactivation by peripheral and vascular tissue enzymes at the site of drug delivery and during travel through the venous blood stream. In order to deliver a dose that will yield an acceptable quantity for treating disease with subcutaneous and intravenous administration of an active agent, dosing regimens will always have to account for the inactivation of the active agent by peripheral and vascular venous tissue and ultimately the liver.

SUMMARY

Method of treating obesity associated with type 1 and type 2 diabetes and including, Prader-Willi syndrome is disclosed. In one embodiment, a method of treating binge eating disorders, obesity as a result of binge eating disorders, and associated symptoms is disclosed.

In particular, the method of treating obesity utilizes a drug delivery system which is designed for drug delivery to the lungs, including by inhalation, for rapid delivery and onset of action of the active agent being delivered to target tissues using the arterial circulation in the lungs. In this method, the active agent can reach its target site in a therapeutically effective manner. In one embodiment, the method comprises administering to an obese subject a stable pharmaceutical composition comprising, an active agent for treating obesity into the systemic circulation of the subject by pulmonary inhalation using a dry powder inhaler. In one embodiment, the method comprises providing to a patient in need of treatment a dry powder inhaler comprising the active agent in a stable dry powder formulation, and administering the active agent by oral inhalation to the patient.

In one embodiment, the drug delivery system comprises a dry powder inhaler comprising a diketopiperazine-based drug formulation for delivering therapeutically effective amounts of at least one active agent, including, a peptide and/or protein-based active ingredients for treating obesity. The inhalation method provides advantages over typical methods of drug delivery, such as, oral tablet and subcutaneous and intravenous injectable drug products that are sensitive to degradation and/or enzymatic deactivation.

In certain embodiments disclosed herein, a method for providing an active agents to a patient in need thereof is disclosed comprising, selecting one or more active agent subject to degradation in the patient, wherein effectiveness of the active agent is reduced by the degradation or deactivation; wherein the active agent is combined with a diketopiperazine to produce a pharmaceutical composition suitable for pulmonary inhalation; and providing the pharmaceutical composition to the patient so that the active agent reaches the target site with substantially no degradation or no deactivation in therapeutically effective amounts.

Also disclosed herein is a method of treating a disease or disorder comprising, selecting a patient to be treated with, or a patient with a condition treatable with an active agent typically provided only as an injectable; replacing the injectable with an inhalation system and providing the patient with an inhaler comprising the one or more active agents in a stable dry powder composition for treating the disease or disorder; wherein the stable dry powder composition comprises the active agent and a diketopiperazine; and administering the stable dry powder composition to the patient by pulmonary inhalation; thereby treating the disease or condition.

In one particular embodiment, a method for treating hyperglycemia in an obese subject with, or without type 2 diabetes mellitus is disclosed. The method comprises, administering to a subject in need of treatment a dry powder composition comprising, a diketopiperazine, including fumaryl diketopiperazine and an active agent, wherein the active agent comprises at least one endocrine hormone for stimulating a decrease in blood glucose levels. In embodiments herewith, the endocrine hormone can be selected from the group comprising glucagon-like peptide -1 (GLP-1), glucose-dependent insulinotropic polypeptide (GIP), amylin, an amylin mimetic, or an analog, or derivative thereof, or combinations thereof.

In an exemplary embodiment, the method of treating obesity in an subject including, a subject diagnosed with Prader-Willi syndrome, the method comprises, providing to the subject in need thereof, a dry powder composition comprising a diketopiperazine, including a diketopiperazine having the formula:

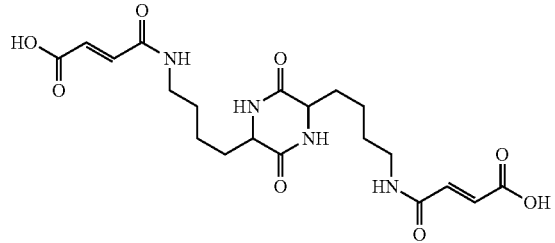

Formula 1 and an peptide hormone, including, amylin, an amylin analog, or an amylin mimetic, including, Symlin® or pramlintide acetate, and administering to the subject the dry powder composition from an oral dry powder inhaler. In this embodiment, the dry powder composition can be administered either alone, and/or in combination with a dry powder composition comprising insulin and fumaryl dikepiperazine. In certain embodiments, a combination therapy with insulin comprises administering an insulin composition separately, subsequently, or concurrently with the Pramlintide administration, wherein the insulin composition is a rapid acting insulin for rapidly reducing blood glucose levels, and wherein the subject's hyperglycemia can be more tightly control. In this embodiment, blood glucose levels in the subject to be treated are greater than 120 mg/dL, or greater than 140 mg/dL and the insulin can be administered by inhalation or by other routes of administration.

In another exemplary embodiment, the method of treating obesity and hyperglycemia resulting from binge eating in a subject diagnosed with Prader-Willi syndrome and/or diagnosed with type 2 diabetes mellitus, the method comprising, providing the subject an inhaler comprising a dry powder composition comprising a peptide hormone, for example, amylin, an amylin mimetic, including, Symlin® or pramlintide acetate, or an analog thereof, or combinations thereof, and administering to the subject the dry powder composition from the inhaler in a single inhalation. In this and other embodiments, the dry powder composition is delivered to the subject with an oral inhalation system which comprises a high resistance dry powder inhaler immediately prior to the beginning of a meal, or at mealtime. In one embodiment, the content of the pramlintide acetate in the composition can comprise from about 0.5% (wt %) to about 50% (wt %), and can be delivered using an oral inhalation system comprising a multiple use inhaler which can be adapted with replaceable cartridges configured to contain a single dose of the dry powder composition. Alternatively, the oral inhalation system can comprise a disposable inhaler containing a single dose of the dry powder composition. In this and other embodiments, the dry powder comprising pramlintide is administered at meal time, or just before eating a meal or a snack in amounts ranging from about 0.01 mg to 5 mg of pramlintide acetate in the composition.

In an embodiment, a method for treating obesity in an obese subject with Prader-Willi disorder and having type 2 diabetes mellitus is disclosed. The method comprises, selecting a subject diagnosed with Prader-Willi disease and in need of treatment for type 2 diabetes mellitus, and administering an inhalable dry powder composition comprising, a diketopiperazine, including fumaryl diketopiperazine and one or more active agents, including amylin, an amylin mimetic, including Symlin® or pramlintide acetate, or an analog thereof, or combinations thereof.

In alternative embodiments, the method for treating obesity and hyperglycemia in patients with type 1, type 2, and/or Prader-Willi syndrome comprises a combination therapy, which comprises administering at mealtime a dry powder composition comprising pramlintide acetate by oral inhalation, and optionally, administering a second medication or drug, for example, an insulin, or an analog thereof which can be provided by inhalation, or other routes of administration, including, injections. In one particular embodiment, the combination therapy can comprise administering to the subject a dry powder composition comprising the pramlintide acetate and a dry powder composition comprising insulin, wherein the dry powder comprising pramlintide acetate and dry powder comprising insulin can be administered independently in subsequent dosages to one another or simultaneously as a blend of the two dry powders by oral inhalation. In one embodiment, the dry powder composition can be formed with the diketopiperazine by adding the two active ingredients during formation of the dry powders.

In an alternate embodiment herewith, the method of treatment can comprise providing a subject with independently formulated dry powder compositions of pramlintide acetate and insulin in separate containers which can be administered from separate inhalers. In one embodiment, a composition comprising pramlintide acetate and insulin can be provided in the same dry powder, which is formulated together as a combination product from a suspension comprising particles of fumaryl diketopiperazine and the two active agents, or as a mixture of blended powders which were initially formed separately. In this and other embodiments, the dry powder or mixture/blend of dry powder can comprise 0.01 mg to 5 mg of pramlintide acetate in the composition. In embodiments herewith, dry powder blends of pramlintide acetate and insulin can be administered depending on the patient's needs.

In alternative embodiments, the method of treating a Prader-Willi syndrome comprises a combination therapy comprising administering a dry powder composition comprising a fumaryl diketopiperazine and pramlintide acetate by oral inhalation with a high resistant dry powder inhaler, and optionally, administering a second medication or drug, for example, a rapid acting insulin or a selective serotonin receptor agonist, or serotonin reuptake inhibitor such as fluoxetine and duloxetine, which can be given by oral inhalation, or other routes of administration such as oral tablets or injections. In one embodiment, the combination therapy can comprise a dry powder composition comprising the pramlintide acetate and one or more additional drug(s) that can be also administered by oral inhalation separately, as a blended mixture of powders or processed as a single formulation comprising the two or more active ingredients.

In one embodiment, the method for treating obesity related to Prader-Willi syndrome comprises providing a drug delivery system to a subject which comprises a dry powder inhaler comprising a composition comprising, fumaryl diketopiperazine and an amylin, an amylin mimetic, or amylin analog and optionally, a small molecule including, a molecule that binds to serotonin (5-Hydroxytryptamine) receptors and/or are serotonin receptor agonists. Small molecules can be provided in dry powder form, separately, simultaneously or as needed, and include, triptans, for example, sumatriptan, zolmitriptan, rizatriptan, naratriptan, almotriptan, eletriptan and frovatriptan.

In particular embodiments, the diketopiperazine is 2,5-diketo-3,6-di(4-X-aminobutyl)piperazine; wherein X is selected from the group consisting of succinyl, glutaryl, maleyl, and fumaryl; or a pharmaceutically acceptable salt thereof. In another embodiment, the pharmaceutical composition is an inhalable dry powder formulation.

In yet another embodiment, the inhalable dry powder formulation further comprises amylin or an amylin mimetic, including pramlintide acetate and a pharmaceutically acceptable carrier or excipient. In certain embodiments herewith, the dry powder composition can optionally comprise an amino acid such an aliphatic amino acid, for example, alanine, glycine, leucine, isoleucine, norleucine at amounts ranging from about 0.5% to about 50% by weight. In one particular embodiment, the dry powder composition comprises the amino acid L-leucine.

In some embodiments, a pharmaceutical composition may comprise preformed crystalline or crystalline composite particles or an amorphous powder of fumaryl diketopiperazine, wherein the particles may comprise a diketopiperazine, and at least pramlintide and optionally, an aliphatic amino acid, which aliphatic amino acid may be incorporated into, adhered to, complexed with, coated, or adsorbed onto a diketopiperazine particles. In particular embodiments, a diketopiperazine particle may be coated with amylin, an amylin mimetic, including, pramlintide acetate or combinations thereof, and an aliphatic amino acid.

In another embodiment of the disclosed method, the step of administering the composition to the patient comprises pulmonary administration of the dry powder composition by oral inhalation using a breath powered, dry powder inhaler with a capsule or container, wherein the container can be a cartridge, such as a unit dosing cartridge for a reusable inhaler, or a single use inhaler. In this and other embodiments, the dry powder inhaler system comprises a high resistance dry powder inhaler having air flow resistance values through its conduits in use of about 0.0065 to about 0.200 $\sqrt{(\kappa Pa)}/L$ per minute, wherein the dry powder inhaler in use has an air flow distribution entering through the inhaler of from about 20% to about 60% through the container, which inhaler system generates peak inhalation pressure differentials of about 2 κPa to about 20 κPa, and peak flow rates of between about 7 to about 70 liters per minute.

Disclosed herein is also a method for preventing or reducing adverse effects such as profuse sweating, nausea and vomiting, which normally are associated with subcutaneous and intravenous administration of pramlintide acetate therapy. In particular, the method comprises the administration of a molecule into the pulmonary circulation such as by inhalation into pulmonary alveolar capillaries using a dry powder drug delivery system.

In one embodiment, a method is provided for the treatment of hyperglycemia and/or diabetes in a patient, comprising the step of administering prandially to a patient in need of treatment an inhalable dry powder formulation, comprising a therapeutically effective amount of a pramlintide acetate molecule alone or in combination with insulin, wherein the administration does not result in at least one side effect selected from the group consisting of nausea, vomiting and profuse sweating.

In one embodiment, a method is provided for reducing glucose levels in a type 1 or type 2 diabetic patient suffering with hyperglycemia, the method comprising the step of administering to the patient in need of treatment an inhalable crystalline dry powder formulation or a crystalline composite formulation for pulmonary administration at mealtime comprising a therapeutically effective amount of pramlintide and fumaryl diketopiperazine and/or a pharmaceutically acceptable salt thereof, and optionally, a pharmaceutically-acceptable excipient.

In another embodiment, the inhalable dry powder composition comprising pramlintide may lack inhibition of gastric emptying upon administration. In one embodiment, a kit is provided for the treatment of diabetes and/or hyperglycemia comprising: a) a blister configured to have at least one of a medicament container, capsule, or cartridge operably configured to fit into a dry powder inhaler and containing a dry powder formulation comprises a pramlintide molecule, and a diketopiperazine of the formula: 2,5-diketo-3,6-di(4-X-aminobutyl)piperazine; wherein X is selected from the group consisting of succinyl, glutaryl, maleyl, and fumaryl, or salt thereof, and b) an inhalation device operably configured to receive/hold and securely engage the container, capsule or cartridge.

In another embodiment, a kit is provided for the treatment of hyperglycemia in a type 2 diabetes, obese, patient, which comprises a pulmonary drug delivery system, comprising: a) a blister configured to hold at least one of a medicament container, capsule or cartridge operably configured to fit into a dry powder inhaler and capable of containing and delivering a dry powder formulation comprising at least a pramlintide molecule, and a diketopiperazine of the formula: 2,5-diketo-3,6-di(4-X-aminobutyl)piperazine; wherein X is selected from the group consisting of succinyl, glutaryl, maleyl, and fumaryl, or salt thereof, and b) an inhalation device operably configured to adapt and securely engage the cartridge and deliver the dry powder formulation to the patient in use.

In another embodiment, a method to induce a pulsatile insulin release in a subject having type 2 diabetes is provided. The method comprises administering to a subject diagnosed with type 2 diabetes and exhibiting a blood glucose level greater than 7 mmol/L, greater than 9 mmol/L, greater than 10 mmol/L or greater than 11 mmol/L, an inhalable dry powder formulation, comprising a therapeutically effective amount of a pramlintide molecule and a diketopiperazine; wherein the pramlintide molecule in the dry powder formulation is administered to the patient in one or more doses, which doses are effective to slow the rate of appearance of glucose in blood after eating by slowing down gastric emptying, inhibiting glucagon action and thus gluconeogenesis upon administration of the formulation. In embodiments wherein the dry powder formulation is administered in more than one doses, the intervals between dosing depends on the patient and can range from prandially at time 0 or immediately before eating with the first dose, and to about 8 hours postprandially. In one embodiment, for example, the method comprises administering to a patient a first dose of the dry powder formulation prandially, and another dose of the formulation at 15, 30, 45, 60, 120, and/or 150 minutes postprandially. In this and other embodiments, the inhalable dry powder formulation can be provided to the patient using a dry powder inhalation system adapted with a cartridge containing the dry powder formulation.

In an alternate embodiment, a method is provided for the treatment of obesity related to Prader Willi Syndrome and diabetes; the method comprising administering to a patient in need of treatment a first dose of a formulation comprising a dry powder comprising a diketopiperazine, for example, fumaryl diketopiperazine, and Pramlintide in combination with a second dose of a composition comprising oxytocin, insulin, or a serotonin receptor agonist including, triptans, duloxetine or a pharmaceutically acceptable derivative or salt thereof. In one embodiment, the second dose may be administered by alternative routes of administration, including, injectables or oral formulations, or can be administered as an inhalable powder comprising a diketoperazine.

DEFINITION OF TERMS

Prior to setting forth the invention, it may be helpful to provide an understanding of certain terms that will be used hereinafter:

Active Agents: As used herein "active agent" refers to drugs, pharmaceutical substances and bioactive agents. Active agents can be small molecules, which are typically less than about 1,000 in molecular weight, do not necessarily have repeated units. Active agents can also be organic macromolecules including nucleic acids, synthetic organic compounds, polypeptides, peptides, proteins, polysaccharides and other sugars, and lipids. Peptides, proteins, and polypeptides are all chains of amino acids linked by peptide bonds. Peptides are generally considered to be less than 40 amino acid residues, but may include more. Proteins are polymers that typically contain more than 40 amino acid residues. The term polypeptide as is known in the art and as used herein, can refer to a peptide, a protein, or any other chain of amino acids of any length containing multiple peptide bonds, though generally containing at least 10 amino acids. The active agents can fall under a variety of biological activity classes, such as vasoactive agents, neuroactive agents, hormones, anticoagulants, immunomodulating agents, cytotoxic agents, antibiotics, antiviral agents, antigens, and antibodies. In some instances, the terms "drug," "active ingredient" and "active agent" are used interchangeably.

Diketopiperazine: As used herein, "diketopiperazine" or "DKP" includes diketopiperazines, derivatives, analogs and modifications thereof, in both the salt and non-salt form of any of the foregoing, falling within the scope of the general Formula 1, wherein the ring atoms $E_1$ and $E_2$ at positions 1 and 4 are either O or N and at least one of the side-chains $R_1$ and $R_2$ located at positions 3 and 6 respectively contains a carboxylic acid (carboxylate) group. Compounds according to Formula 1 include, without limitation, diketopiperazines, diketomorpholines and diketodioxanes and their substitution analogs.

Formula 1

Diketopiperazines, in addition to making aerodynamically suitable microparticles, can also facilitate the delivery of active agents by rapidly dissolving at physiologic pH thereby releasing the active agent and speeding its absorption into the circulation. Diketopiperazines can be formed into particles that incorporate a drug or particles onto which a drug can be adsorbed. The combination of a drug and a diketopiperazine can impart improved drug stability. These particles can be administered by various routes of administration. As dry powders these particles can be delivered by inhalation to specific areas of the respiratory system, depending on particle size. Additionally, the particles can be made small enough for incorporation into an intravenous suspension dosage form. Oral delivery is also possible with the particles incorporated into a suspension, tablets or capsules.

In one embodiment, the diketopiperazine is 3,6-di(fumaryl-4-aminobutyl)-2,5-diketopiperazine (fumaryl diketopiperazine, FDKP). The FDKP can comprise microparticles in its acid form or salt forms which can be aerosolized or administered in a suspension.

In another embodiment, the DKP is a derivative of 3,6-di(4-aminobutyl)-2,5-diketopiperazine, which can be formed by (thermal) condensation of the amino acid lysine. Exemplary derivatives include 3,6-di(succinyl-4-aminobutyl)-, 3,6-di(maleyl-4-aminobutyl)-, 3,6-di(glutaryl-4-aminobutyl)-, 3,6-di(malonyl-4-aminobutyl)-, 3,6-di(oxalyl-4-aminobutyl)-, and 3,6-di(fumaryl-4-aminobutyl)-2,5-diketopiperazine. The use of DKPs for drug delivery is known in the art (see for example U.S. Pat. Nos. 5,352,461, 5,503,852, 6,071,497, and 6,331,318, each of which is incorporated herein by reference for all that it teaches regarding diketopiperazines and diketopiperazine-mediated drug delivery). The use of DKP salts is described in U.S. Pat. No. 7,820,676, which is hereby incorporated by reference for all it teaches regarding diketopiperazine salts. Pulmonary drug delivery using DKP microparticles is disclosed in U.S. Pat. No. 6,428,771, which is hereby incorporated by reference in its entirety. Further details related to adsorption of active agents onto crystalline DKP particles can be found in U.S. Pat. Nos. 7,799,344 and 7,803,404, which are hereby incorporated by reference in their entirety.

Drug delivery system: As used herein, "drug delivery system" refers to a system for delivering one or more active agents of a composition.

Dry powder: As used herein, "dry powder" refers to a fine particulate composition that is not suspended or dissolved in a propellant, carrier, or other liquid. It is not meant to necessarily imply a complete absence of all water molecules. The powder can be a crystalline powder, an amorphous powder, or a crystalline composite powder.

Endocrine disease: The endocrine system is an information signal system that releases hormones from the glands to provide specific chemical messengers which regulate many and varied functions of an organism, e.g., mood, growth and development, tissue function, and metabolism, as well as sending messages and acting on them. Diseases or disorders of the endocrine system include, but are not limited to diabetes mellitus, thyroid disease, and obesity. Endocrine disease can be due to genetic abnormalities and can be characterized by dysregulated hormone release (a productive pituitary adenoma), inappropriate response to signaling (hypothyroidism), lack or destruction of a gland (diabetes mellitus type 1, diminished erythropoiesis in chronic renal failure), reduced responsiveness to signaling (insulin resistance of diabetes mellitus type 2), or structural enlargement in a critical site such as the neck (toxic multinodular goiter). Hypofunction of endocrine glands can occur as result of loss of reserve, hyposecretion, agenesis, atrophy, or active destruction. Hyperfunction can occur as result of hypersecretion, loss of suppression, hyperplastic, or neoplastic change, or hyperstimulation. The term endocrine disorder encompasses metabolic disorders.

Excursion: As used herein, "excursion" can refer to blood glucose concentrations that fall either above or below a pre-meal baseline or other starting point. Excursions are generally expressed as the area under the curve (AUC) of a plot of blood glucose over time. AUC can be expressed in a variety of ways. In some instances there will be both a fall below and rise above baseline creating a positive and negative area. Some calculations will subtract the negative AUC from the positive, while others will add their absolute values. The positive and negative AUCs can also be considered separately. More sophisticated statistical evaluations can also be used. In some instances it can also refer to blood glucose concentrations that rise or fall outside a normal range. A normal blood glucose concentration is usually between 70 and 110 mg/dL from a fasting individual, less than 120 mg/dL two hours after eating a meal, and less than 180 mg/dL after eating. While excursion has been described here in terms of blood glucose, in other contexts the term may be similarly applied to other analytes.

Hyperglycemia: As used herein, "hyperglycemia" is a higher than normal fasting blood glucose concentration, usually 120 mg/dL or higher. In some studies hyperglycemic episodes were defined as blood glucose concentrations exceeding 280 mg/dL (15.6 mM).

Hypoglycemia: As used herein, "hypoglycemia" is a lower than normal blood glucose concentration, usually less than 63 mg/dL 3.5 mM), Clinically relevant hypoglycemia is defined as blood glucose concentration below 63 mg/dL or causing patient symptoms such as hypotonia, flush and weakness that are recognized symptoms of hypoglycemia and that disappear with appropriate caloric intake. Severe hypoglycemia is defined as a hypoglycemic episode that required glucagon injections, glucose infusions, or help by another party.

In proximity: As used herein, "in proximity," as used in relation to a meal, refers to a period near in time to the beginning of a meal or snack.

Microparticles: As used herein, the term "microparticles" includes particles of generally 0.5 to 100 microns in diameter and particularly those less than 10 microns in diameter. Various embodiments will entail more specific size ranges. The microparticles can be assemblages of crystalline plates with irregular surfaces and internal voids as is typical of those made by pH controlled precipitation of the DKP acids. In such embodiments the active agents can be entrapped by the precipitation process or coated onto the crystalline surfaces of the microparticle. The microparticles can also be spherical shells, or collapsed spherical shells comprising DKP salts with the active agent dispersed throughout. Typically such particles can be obtained by spray drying a co-solution of the DKP and the active agent. The DKP salt in such particles can be amorphous. In one embodiment, the particles can be made by a process wherein the particles do not self-assemble in suspension and the crystalline plates formed without the presence of a surfactant form substantially spherical particles and/or hollow spheres comprising outer crystalline shells upon spray-drying that give rise to a crystalline composite powder. The forgoing descriptions should be understood as exemplary. Other forms of microparticles are contemplated and encompassed by the term.

Obesity: is a condition in which excess body fat has accumulated to such an extent that health may be negatively affected. Obesity is typically assessed by BMI (body mass index) with BMI of greater than 30 kg/m$^2$.

Peripheral tissue: As used herein, "peripheral tissue" refers to any connective or interstitial tissue that is associated with an organ or vessel.

Periprandial: As used herein, "periprandial" refers to a period of time starting shortly before and ending shortly after the ingestion of a meal or snack.

Postprandial: As used herein, "postprandial" refers to a period of time after ingestion of a meal or snack. As used herein, late postprandial refers to a period of time 3, 4, or more hours after ingestion of a meal or snack.

Prandial: As used herein, "prandial" refers to a meal or a snack.

Preprandial: As used herein, "preprandial" refers to a period of time before ingestion of a meal or snack.

Pulmonary inhalation: As used herein, "pulmonary inhalation" is used to refer to administration of pharmaceutical preparations by inhalation so that they reach the lungs and in particular embodiments the alveolar regions of the lung. Typically inhalation is through the mouth, but in alternative embodiments in can entail inhalation through the nose.

DETAILED DESCRIPTION

There is disclosed a method for the treatment of a disease or disorder which utilizes a drug delivery system that effectively delivers an active agent to the pulmonary circulation so that the active agent enters the pulmonary circulation and can be delivered in a therapeutic amount to the site(s) of action. The methods of treatment of disease or disorders comprise, administering to a patient in need of treatment a formulation, which can deliver the active agent directly into the pulmonary circulation, and thereby to the arterial circulation, and can avoid degradation of the active agent such as peptides, by enzymes or other mechanisms in the local peripheral and/or vasculature tissues of the lungs. In one embodiment, the method comprises the effective therapeutic delivery of active agents using a drug delivery system which allows for very rapid lung absorption of the active agent into the circulation and increases its effective bioavailability. In this embodiment, lower dosages of an active agent can be delivered by this method of administration. In similar embodiments, effective doses of an active agent can be achieved where they were not feasible by other modes of administration.

In embodiments herein, there is disclosed a method for the treatment of disease, including, endocrine disease, such as diabetes, hyperglycemia and obesity. The inventors have identified the need to deliver drugs directly to the systemic circulation, in particular, the arterial circulation in a noninvasive fashion so that the drug reaches the target organ(s) prior to returning through the venous system. This approach may paradoxically result in a higher peak target organ exposure to active agents than would result from a comparable administration by injections, including, intravenous, subcutaneous or other parenteral route. A similar advantage can be obtained versus oral administration as, even with formulations providing protection from degradation in the digestive tract, upon absorption the active agent also enters the venous circulation.

In one embodiment, the drug delivery system can be used with any type of active agent that is rapidly metabolized and/or degraded by direct contact with the local degradative enzymes or other degradative mechanisms, for example, oxidation, phosphorylation or any modification of the molecules including small molecules, proteins or peptides, in the peripheral or vascular venous tissue encountered with other routes of administration such as oral, intravenous, transdermal, and subcutaneous administration. In this embodiment, the method can comprise the step of identifying and selecting an active agent which activity is metabolized or degraded by oral, subcutaneous or intravenous administration. For example, due to peptide lability, subcutaneous injection of, for example, GLP-1 has not led to effective levels of GLP-1 in the blood. This contrasts with peptides such as insulin which can be delivered effectively by such modes of administration. In these embodiments, the method of administering a drug is advantageous for, for example, rapid onset of treatment since the drug can reach the target organ more rapidly through the arterial circulation without invasive therapy such as injections.

In certain embodiments, the method of treatment of a disease or disorder comprises the step of selecting a suitable carrier for inhalation and delivering an active substance to pulmonary alveoli. In this embodiment, the carrier can be associated with one or more active agents to form a drug/carrier complex which can be administered as a composition that avoids rapid degradation of the active agent in the peripheral and vascular venous tissue of the lung. In one embodiment, the carrier is a diketopiperazine, and in particular, a compound having the formula I, 3,6-bis(N-fumaryl-4-aminobutyl)-2,5-diketopiperazine:

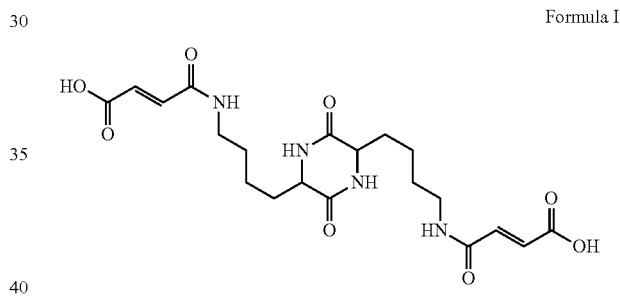

Formula I

The method described herein can be utilized to deliver many types of active agents, including small molecules and biologicals. In particular embodiments, the method utilizes a drug delivery system that effectively delivers a therapeutic amount of an active agent, including, small molecules or peptide hormones, rapidly into the arterial circulation. In one embodiment, the one or more active agents include, but are not limited to peptides such as pramlintide, proteins, lipokines, small molecule pharmaceuticals, nucleic acids and the like, which is/are sensitive to degradation or deactivation; formulating the active agent into a dry powder composition comprising a diketopiperazine and delivering the active agent(s) into the systemic circulation by pulmonary inhalation using a cartridge and a dry powder inhaler. In one embodiment, the method comprises selecting a peptide that is sensitive to enzymes in the local vascular or peripheral tissue of, for example, the dermis, or lungs. The present method allows the active agent to avoid or reduce contact with peripheral tissue, venous or liver metabolism/degradation.

In one embodiments, the method of treatment is directed to the treatment of diabetes, hyperglycemia and/or obesity using, for example, dry powder formulations comprising amylin, amylin analogs, amylin mimetics, including pramlintide, alone or in combination with insulin. In a particular embodiment, the method of treating disease comprises the treatment of hyperglycemia in subjects with Prader-Willi syndrome and having type 2 diabetes mellitus.

In an exemplary embodiment, a method for treating obesity, diabetes and/or hyperglycemia comprises administering to a patient in need of treatment a dry powder composition or formulation comprising pramlintide, which slows the rate at which food absorption occurs, including glucose absorption from the intestine, and reduces the production of glucose by the liver by inhibiting the action of glucagon. In one embodiment, the method comprises administering a dry powder composition comprising, amylin or an amylin mimetic, including pramlintide for reducing appetite and for lowering blood glucose levels; inhibiting gluconeogenesis and reducing unwanted side effects such as profuse sweating, nausea, and vomiting. In one embodiment, the method of treating disease can be applied to a patient, including a mammal, suffering with obesity, type 2 diabetes mellitus and/or hyperglycemia at dosages ranging from about 0.01 to about 5 mg (wt %) of pramlintide in the formulation in a single dose.

The method of treating hyperglycemia, diabetes, and/or obesity can be designed so that the patient can receive at least one dose of a pramlintide inhalable formulation in proximity to a meal or snack. In this embodiment, the dose of pramlintide can be selected depending on the patient's requirements. In one embodiment, pulmonary administration of pramlintide can comprise a pramlintide dose greater than 0.3 mg for example, in treating patients with type 2 diabetes.

In embodiments of the invention, the pramlintide formulation is administered by pulmonary inhalation by providing the pramlintide in a dry powder formulation for oral inhalation. In one embodiment, the dry powder formulation is a stable composition and can comprise microparticles which are suitable for inhalation and which dissolve rapidly in the alveoli of the lung, which rapidly delivers pramlintide to the pulmonary circulation. Suitable particle sizes for pulmonary administration can be less than 10 μm in diameter, and preferably less than 5 μm. Exemplary particle sizes that can reach the pulmonary alveoli range from about 0.5 μm to about 5.8 μm in diameter. Such sizes refer particularly to aerodynamic diameter, but often also correspond to actual physical diameter as well. Such particles can reach the pulmonary capillaries and can avoid extensive contact with the peripheral tissue in the lung. In this embodiment, the drug can be delivered to the arterial circulation in a rapid manner and avoid degradation of the active ingredient by enzymes or other mechanisms prior to reaching its target or site of action in the body. In one embodiment, dry powder compositions for pulmonary inhalation comprising microparticles of pramlintide and fumaryl diketopiperazine, wherein from about 35% to about 75% of the microparticles in the composition have an aerodynamic diameter of less than 5.8 μm.

The methods of delivery presented in various embodiments of the present invention can provide a more direct path to an active agent's site of action. Thus in addition to the avoidance of degradation, though in some instances still in part due to it, the biodistribution of the active agent can differ from that achieved with modes of delivery that entail absorption into and travel through the venous circulation prior to reaching sites of action in the body.

In one embodiment, the dry powder formulation for use with the methods comprises particles comprising a pramlintide molecule and a diketopiperazine or a pharmaceutically acceptable salt thereof. In embodiments herewith, the diketopiperazine can be a crystalline powder, a crystalline composite powder of an amorphous powder, in particular, made from fumaryl diketopiperazine.

In an exemplary embodiment, the method comprises the administration of a dry powder comprising the peptide hormone amylin, an amylin mimetic, including, pramlintide to a patient for the treatment of hyperglycemia and/or diabetes, and obesity. The method comprises administering to a patient in need of treatment an effective amount of an inhalable composition or formulation comprising a dry powder formulation comprising amylin, amylin mimetic, including pramlintide which stimulates the rapid reduction of blood glucose levels and inhibition of glucagon action and also reducing unwanted side effects, including, profuse sweating, nausea, and vomiting. In one embodiment, the method of treating disease can be applied to a patient, including a mammal, suffering with type 1, type 2 diabetes mellitus, Prader-Willi syndrome and/or hyperglycemia at dosages ranging from about 0.01 mg to about 5 mg, from about 0.02 mg to about 3 mg, or from about 0.05 mg to about 2 mg of pramlintide in the dry powder formulation. In one embodiment, the patient or subject to be treated is a human which can be treated with a dose of up to 50 mg in total powder content. The pramlintide can be administered immediately before a meal (preprandially), at mealtime (prandially), and/or at about 15, 30, 45, 90 minutes after a meal (postprandially). In one embodiment, a single dose of pramlintide can be administered immediately before a meal and another dose can be administered after a meal.

In embodiments described herein, pramlintide can be administered at mealtime (in proximity in time to a meal or snack). In this embodiment, pramlintide exposure can be limited to the postprandial period so it does not cause the long acting effects of current therapies, which can lead to hypoglycemia.

In one embodiment, the drug delivery system can be utilized in a method for treating obesity so as to control or reduce food consumption in a subject such as a patient diagnosed with Prader-Willi syndrome. In this embodiment, patients in need of treatment or suffering with obesity and hyperglycemia resulting from binge eating are administered a therapeutically effective amount of an inhalable composition or formulation comprising pramlintide alone or in combination with a rapid acting inhalable insulin composition using a dry powder inhaler. In alternate embodiments, the patient can be administered other appetite suppressant active agent, including, oxyntomodulin, peptide YY(3-36), or combinations thereof, or analogs thereof, with or without additional appetite suppressants known. In this embodiment, the method is targeted to reduce food consumption, inhibit food intake in the patient, decrease or suppress appetite, and/or control body weight.

In one embodiment, the inhalable formulation comprises a dry powder formulation comprising the above-mentioned active ingredient with a diketopiperazine, including 2,5-diketo-3,6-di(4-X-aminobutyl)piperazine; wherein X is selected from the group consisting of succinyl, glutaryl, maleyl, and fumaryl, or a salt of the diketopiperazine. In this embodiment, the inhalable formulation can comprise microparticles for inhalation comprising the active ingredient with the aerodynamic characteristics as described above. In one embodiment, the amount of active ingredient can be determined by one of ordinary skill in the art, however, the present microparticles can be loaded with various amounts of active ingredient as needed by the patient. For example, for pramlintide acetate, the microparticles can comprise from about 0.5% (wt %) to about 50% (wt %) of the pramlintide in the formulation. In certain embodiments, the inhalable formulations can comprise from about 1% (wt %) to about 30% (wt %) of the pharmaceutical composition and can also comprise a pharmaceutically acceptable carrier, or excipient, such as a surfactant, such as polysorbate 80. In this embodiment, pramlintide can be administered to the patient from once to about four times a day or as needed by the patient with doses ranging from about 0.01 mg up to about 5 mg in the formulation.

In another embodiment, inhalable pramlintide can be administered with insulin as a combination therapy and given prandially for the treatment of hyperglycemia and/or diabetes. In this embodiment, inhalable pramlintide and insulin can be co-formulated in a dry powder formulation or administered separately to a patient in their own dry powder formulation. In one embodiment, wherein the pramlintide and insulin are co-administered, both active ingredients can be co-formulated, for example, the pramlintide and insulin can be prepared in a dry powder formulation for inhalation using a fumaryl diketopiperazine particle as described above in crystalline, crystalline composite or as an amorphous powder. Alternatively, the pramlintide and insulin can be formulated separately, wherein each formulation is for inhalation and comprise a diketopiperazine particle as describe above. In one embodiment the pramlintide and the insulin formulations can be admixed or blended together in their individual powder form to the appropriate dosing prior to administration. In this embodiment, the insulin can be short-, intermediate-, or long-acting insulin and can be administered prandially. In one embodiment, the insulin is a rapid acting insulin dry powder formulation which can be administered to a patient prandially, simultaneously, or sequentially to an inhalable formulation of pramlintide.

In certain embodiments of the combination therapy for treating obesity, the insulin formulation can be administered by other routes of administration. In this embodiment, the combination therapy can be effective in reducing insulin requirements in a patient to maintain the euglycemic state. In one embodiment, the combination therapy can be applied to patients suffering with obesity and/or type 2 diabetes, which are receiving long acting insulin such as insulin detemir (LEVEMIR®) or insulin glargine (LANTUS®, TUJEO®) which subject need tighter glucose control and can be administered by an inhalation powder also comprising inhalable pramlintide. In this embodiment, rapid acting inhalable pramlintide and a diketopiperazine formulation can be administered in combination with rapid acting inhalable insulin for the treatment of hyperglycemia resulting from diabetes.

In another exemplary embodiment, a method for treating Pader-Willi-syndrome obesity and other symptoms associated with the disorder is disclosed. In one embodiment, the method comprises administering prandially to a subject diagnosed with type 2 diabetes an effective amount of a dry powder of an inhalable composition comprising pramlintide and a diketopiperazine using a dry powder inhaler for delivering to the pulmonary tract, and optionally, administering subsequently, sequentially, or concomitantly, a rapid acting inhalable insulin composition. In this embodiment, the pharmaceutical composition comprises, for example, diketopiperazine microparticles, including, FDKP or an FDKP salt, for example, a divalent salt of FDKP, including disodium FDKP. In this therapy, the subject can be treated, for example, with a drug or a small molecule, including a vasoconstrictor as the active agent which can be administered by other routes of administration. Examples of vasoconstrictors are serotonin receptor agonists, including, tripans such as sumatriptan, almotriptan, eletriptan, frovatriptan, naratriptan, rizatriptan, zolmitriptan and pharmaceutically acceptable salts thereof, including sumatriptan succinate, rizatriptan benzoate, almotriptan malate. In one embodiment, the vasoconstrictor, for example, a triptan can be provided to a patient in need of treatment in amounts ranging from at least about 0.1 mg, at least about 1 mg, at least about 5 mg, about 50 mg or less, about 40 mg or less, about 1 mg to about 50 mg, about 5 mg to about 30 mg, about 10 mg. to about 20 mg, about 1 mg, about 10 mg, about 20 mg, or any amount in a range bounded by, or between, any of these values. An inhalable pharmaceutical composition comprising pramlintide acetate can be administered regularly, including daily, twice daily, thrice daily, etc., and/or may be given as need with mealtime, snacks or whenever the subject eats or develops hyperglycemia. In the combination therapy embodiment, the pramlintide can also be formulated with the small molecule or a serotonin receptor agonist, together, blended or separately provided, however, the small molecule is preferably administered separate in its own dry powder for better management of the patient's needs.

In certain embodiments, the method of treating hyperglycemia in a patient suffering with Prader-Willie Syndrome comprises administering to a subject in need of treatment an inhalable dry powder pharmaceutical composition comprising an effective amount of a pramlintide and a diketopiperazine at mealtime, and optionally, a rapid acting inhalable insulin composition. In one embodiment, the method comprises administering a dry powder pharmaceutical composition by oral inhalation using a dry powder inhaler, comprising the dry powder pharmaceutical composition comprising pramlintide manufactured as unit dose cartridges for use with using a breath powered, dry powder inhalation system. In one embodiment, the inhalable dry powder pharmaceutical composition further comprises a pharmaceutically acceptable carrier or excipient.

In other embodiments, there is provided a method for the treatment of Prader Willie Syndrome, wherein the Pramlintide composition is used in combination with other or one or more pharmaceutically active agents for treating the disease or disorder. In one embodiment the Pramlintide is administered at mealtime in simultaneously, with the administration of a serotonin receptor agonist for treating moderate to severe symptoms associated with Prader-Willi syndrome. In this embodiments, the Pramlintide can be co-formulated with the serotonin receptor agonist and the diketopiperazine in making the dry powders. Alternatively, the Pramlintide inhalation powder is administered separately from the inhaler and the triptan can be in the form of a dry powder or administered by others routes of administration. In some embodiments, the triptans can be co-formulated with the Pramlintide composition or made in its own diketopiperazine dry powder.

In particular embodiments, the method of treating hyperglycemia associated with Prader Willi syndrome in patients also diagnosed with diabetes comprises, administering the a rapid acting insulin in combination with the Pramlintide, wherein the Pramlintide is administered at mealtime and the insulin is administered separately and subsequently at mealtime, prior to or 20 to 120 minutes after the step of administering a pramlintide composition. In one embodiment, the insulin can be co-formulated with Pramlintide and thus administered simultaneously. In one embodiment, the insulin can be administered separately by oral inhalation, or by other modes of administration including, but not limited to injections. In an embodiment, orally inhalable insulin is a rapid acting insulin comprising 3,6-bis(N-fumaryl-4-amniobutyl)-2,5-diketopiperazine in dry powder form, which can be provided in 2 units to 16 units of insulin in a cartridge or capsule and the dry powder content can be delivered to the patient in a single inhalation in amounts up to 50 mg of powder. Therapeutically effective doses of Pramlintide can be up to 3 mg, up to 5 mg, or up to 10 mg depending on the formulation to be provided, e.g., separately or co-formulated.

In alternate embodiments, dry powder comprising a single active ingredient can be made, for example, an insulin dry powder for inhalation and a Pramlintide dry powder for inhalation, and respective amounts of powders can be blended depending on the dose and patients need and administered in a single dose. For example, the method comprises; making a Pramlintide dry powder composition comprising a diketopiperazine; making a dry powder composition comprising insulin; blending the dry powder comprising Pramlintide with a predetermined amount of powder comprising insulin and administering the resultant combined powder to a subject in need of treatment.

EXAMPLES

The following examples are included to demonstrate certain embodiments of the invention. It should be appreciated by those of skill in the art that the techniques disclosed in the examples elucidate representative techniques that function well in the practice of the present invention. However, those of skill in the art should, in light of the present disclosure, appreciate that many changes can be made in the specific embodiments that are disclosed and still obtain a like or similar result without departing from the spirit and scope of the invention.

Example 1

Preparation of Pramlintide Dry Powders

FDKP and acetic acid feed solutions, each containing 0.05 wt % polysorbate 80 (PS80), can be prepared (Table 1) and filtered through separate 0.2 μm inline filters, and adjusted to 15-25° C. The feed solutions can be mixed in a high shear mixer. Tangential flow filtration can be used to concentrate and wash the suspension. A 10% (wt %) solution of pramlintide (or its salt form) can be prepared in a dilute acetic acid solution. A suitable amount of the pramlintide stock solution can be added to the FDKP suspension so that the final dried powder contains 0.5-20% (wt %) pramlintide. The suspension can be flash frozen in liquid nitrogen to form pellets and lyophilized to give bulk pramlintide-loaded FDKP microparticles. Alternately, the suspension can be spray dried to give bulk pramlintide-loaded FDKP microparticles.

TABLE 1

Composition of feed solutions used in suspension preparation

| Feed solution (wt %) | Composition (wt %) |
|---|---|
| 10.5% acetic acid solution | 89% water |
| | 10.5% glacial acetic acid |
| | 0.5% polysorbate 80 solution |
| | (10% in water) |
| 2.5% FDKP solution | 95.4% water |
| | 2.5% FDKP |
| | 1.6% NH$_4$OH |
| | 0.5% polysorbate 80 solution |
| | (10% in water) |

Example 2

Preparation of Pramlintide Crystalline Composite Powders

FDKP and acetic acid feed solutions can be prepared (Table 2) and filtered through separate 0.2 μm inline filters, and adjusted to 15-25° C. The feed solutions can be mixed in a high shear mixer as detailed below. Tangential flow filtration can be used to wash the suspension. Alternately, the suspension can be used without tangential flow filtration. A 10% solution of pramlintide (or its acetate salt form) can be prepared in a dilute acetic acid solution. A suitable amount of the pramlintide stock solution can be added to the FDKP suspension so that the final dried powder contains 0.5-50% pramlintide.

TABLE 2

Composition of feed solutions used in suspension preparation

| Feed solution (wt %) | Composition (wt %) |
|---|---|
| 10.5% acetic acid solution | 89.5% water |
| | 10.5% glacial acetic acid |
| 2.5% FDKP solution | 95.9% water |
| | 2.5% FDKP |
| | 1.6% NH$_4$OH |

In summary, using a dual-feed high shear mixer, equal masses of about 10.5 wt % acetic acid and about 2.5 wt % FDKP solutions at about 16° C. ± about 2° C. can be fed at 2000 psi through a 0.001-in$^2$ orifice. The precipitate was collected in a deionized (DI) water reservoir of about equal mass and temperature. The precipitate was concentrated and washed by tangential flow filtration with deionized water. The suspension can be finally concentrated to about 10% solids based on the initial mass of FDKP. The concentrated suspension can be assayed for solids content by an oven drying method.

For samples containing the active ingredient, i.e., Pramlintide acetate, a suspension of FDKP from above was used to which a Pramlintide stock solution (pramlintide dissolved in 2% (wt %) acetic acid was added to the suspension while mixing, then the suspension pH was titrated with ammonium hydroxide to pH 4.5±0.3. The Pramlintide acetate dissolved in a 2% (wt %) acetic acid stock solution was added gravimetrically with stirring to an FDKP-suspension. The Pramlintide-FDKP suspension was independently dispersed using an external mixing 2-fluid nozzle into a Niro SD-Micro™ Spray Dryer fitted with a high efficiency cyclone. Nitrogen was used as the process gas (25 kg/h) and the atomization fluid (2.8 kg/hr). The suspension was spray-dried to give bulk pramlintide-loaded FDKP microparticles.

For compositions comprising more than one active ingredient, for example, a combination of Pramlintide and insulin, the insulin can be added as a powder to the reaction mixture at the stage wherein the Pramlintide is dissolved in the 2% (wt %) acetic acid solution. The amount of insulin can be added gravimetrically and dissolved with the Pramlintide solution, added directly to the suspension in powder form, or dissolved in its own 2% (wt %) acetic acid solution and added to the mixture for the predetermine amount of insulin needed in units after drying.

While the invention has been particularly shown and described with reference to particular embodiments, it will be appreciated that variations of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. An inhalable dry powder pharmaceutical composition comprising a crystalline, amorphous, or crystalline composite form of fumaryl diketopiperazine having the formula:

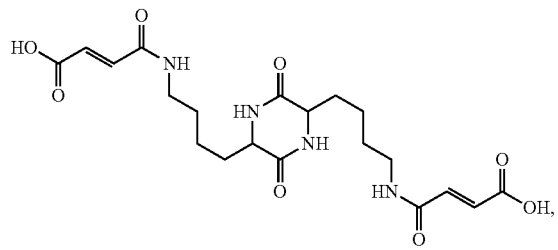 [SMILES: O=C(O)/C=C/C(=O)NCCCCC1NC(=O)C(CCCCNC(=O)/C=C/C(=O)O)NC1=O]

leucine; and pramlintide, wherein said inhalable dry powder pharmaceutical composition in the form of microparticles, and about 35% to about 75% of the microparticles have an aerodynamic diameter of less than 5.8 μm, wherein the composition is effective in the treatment of obesity associated with Prader Willi Syndrome.

2. The dry powder pharmaceutical composition of claim 1, wherein the leucine is about 0.5% to about 30% by weight of the composition.

3. The dry powder pharmaceutical composition of claim 1, wherein the composition is used in combination therapy with a rapid acting insulin, fluoxetidine, duloxetine, or combinations thereof.

4. The dry powder pharmaceutical composition of claim 1, wherein the pramlintide is present up to 10 mg (wt %) of the pharmaceutical composition.

5. The dry powder pharmaceutical composition of claim 1, wherein the pramlintide is present up to 3 mg of dry powder for a single dose.

6. The dry powder pharmaceutical composition of claim 1, wherein the leucine is L-leucine.

7. An inhalable dry powder pharmaceutical composition comprising a crystalline, amorphous, or crystalline composite form of fumaryl diketopiperazine having the formula:

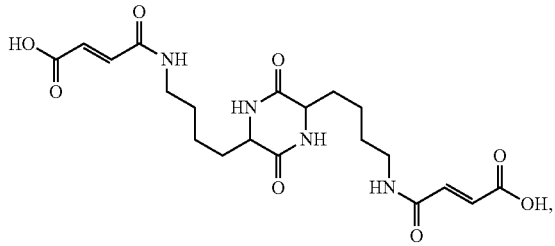 [SMILES: O=C(O)/C=C/C(=O)NCCCCC1NC(=O)C(CCCCNC(=O)/C=C/C(=O)O)NC1=O]

an aliphatic amino acid selected from the group consisting of: alanine, glycine, leucine, isoleucine, norleucine and serine; optionally a pharmaceutically acceptable excipient; and two active agents, said active agents are present consisting of pramlintide and insulin, wherein the insulin is present and comprises up to about 30% (wt %) of the pharmaceutical composition, wherein said inhalable dry powder pharmaceutical composition comprises microparticles, and about 35% to about 75% of the microparticles have an aerodynamic diameter of less than 5.8 μm, and wherein the composition is effective in the treatment of obesity associated with Prader Willi Syndrome.

8. An inhalable dry powder pharmaceutical composition for comprising a crystalline, amorphous, or crystalline composite form of fumaryl diketopiperazine having the formula:

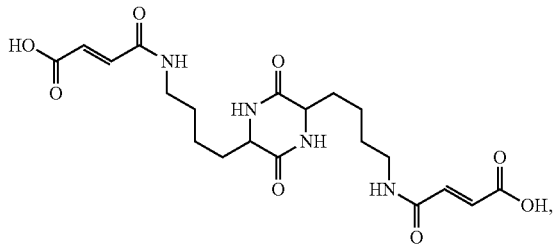 [SMILES: O=C(O)/C=C/C(=O)NCCCCC1NC(=O)C(CCCCNC(=O)/C=C/C(=O)O)NC1=O]

an aliphatic amino acid selected from the group consisting of: alanine, glycine, leucine, isoleucine, norleucine and serine; optionally a pharmaceutically acceptable excipient; and three active agents, said active agents are present consisting of a serotonin receptor agonist, pramlintide, and insulin, wherein the insulin comprises up to about 30% (wt %) of the pharmaceutical composition, wherein said inhalable dry powder pharmaceutical composition comprises microparticles, and about 35% to about 75% of the microparticles have an aerodynamic diameter of less than 5.8 μm, and wherein the composition is effective in the treatment of obesity associated with Prader Willi Syndrome.

9. The dry powder pharmaceutical composition of claim 7 or 8, wherein the insulin is a rapid acting insulin.

10. The dry powder pharmaceutical composition of claim 8, wherein the serotonin receptor agonist is a triptan.

11. The dry powder pharmaceutical composition of claim 10, wherein the triptan is sumatriptan, zolmitriptan, rizatriptan, naratriptan, almotriptan, eletriptan, or frovatriptan.

12. An inhalable dry powder pharmaceutical composition comprising a crystalline, amorphous, or crystalline composite form of fumaryl diketopiperazine having the formula:

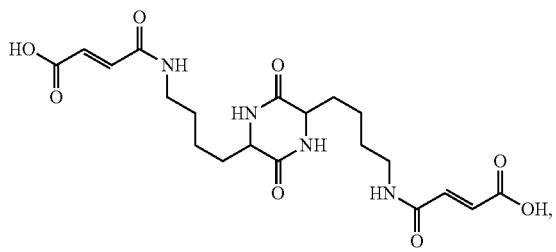

an aliphatic amino acid selected from the group consisting of: alanine, glycine, leucine, isoleucine norleucine and serine; optionally, a pharmaceutically acceptable excipient; and an active agent, said active agent is present consisting of pramlintide, effective in the treatment of obesity associated with Prader Willi Syndrome, wherein said inhalable dry powder pharmaceutical composition comprises microparticles, and about 35% to about 75% of the microparticles have an aerodynamic diameter of less than 5.8 μm.

* * * * *